United States Patent [19]

Steinmetz et al.

[11] Patent Number: 4,705,890

[45] Date of Patent: Nov. 10, 1987

[54] CARBONYLATION PROCESS FOR THE PRODUCTION OF AROMATIC ACIDS

[75] Inventors: Guy R. Steinmetz; Mark Rule, both of Kingsport, Tenn.

[73] Assignee: Eastman Kodak Company, Rochester, N.Y.

[21] Appl. No.: 26,916

[22] Filed: Mar. 17, 1987

[51] Int. Cl.4 ............................................. C07C 51/10
[52] U.S. Cl. .................................................... 562/406
[58] Field of Search ......................................... 562/406

[56] References Cited

U.S. PATENT DOCUMENTS

| | | | |
|---|---|---|---|
| 3,845,121 | 4/1974 | Eubanks et al. | 562/406 |
| 4,134,912 | 1/1979 | Naglieri et al. | 562/406 |
| 4,431,835 | 2/1984 | Gauthier-Lafaye et al. | 562/406 |
| 4,654,436 | 3/1987 | Lane et al. | 562/406 |

Primary Examiner—Paul J. Killos
Attorney, Agent, or Firm—Charles R. Martin; William P. Heath, Jr.

[57] ABSTRACT

Disclosed is a process for production of aromatic carboxylic acids by the carbonylation of aromatic iodides in the presence of a ruthenium catalyst, a Bronsted base, and an iodide promoter.

13 Claims, No Drawings

CARBONYLATION PROCESS FOR THE PRODUCTION OF AROMATIC ACIDS

DESCRIPTION

This invention relates to a novel carbonylation process for the production of aromatic carboxylic acids. More particularly, this invention relates to a process for the carbonylation of aromatic iodides with carbon monoxide in the presence of a ruthenium catalyst, a Bronsted base, and an iodide promoter to prepare aromatic carboxylic acids.

The preparation of carboxylic acid derivatives by carbonylation of aromatic halides catalyzed by Group VIII metal compounds is well known in the art. One such process is described in U.S. Pat. No. 2,640,071 whereby carboxylic acid derivatives are obtained from aromatic halides in a strong base reaction medium using nickel complexes as catalyst at high reaction temperatures of 250°–450° C. and a carbon monoxide pressure of 300 to 1,000 atmospheres. A typical example is the conversion of p-dichlorobenzene to dialkyl terephthalate at 345° C. and 350 atmospheres of carbon monoxide in the presence of a catalytic amount of nickel. This process requires both high tempeatures and pressure.

Another carbonylation process for preparing carboxylic acid derivatives known in the art is described in U.S. Pat. No. 3,988,358 whereby aromatic carboxylic acid esters are prepared from aromatic halides by the reaction of a starting material such as bromobenzene in a basic reaction medium with an alcohol, such as butanol, and carbon monoxide in the presence of an expensive palladium catalyst complexed a ligand such as a tertiary amine or phosphines, for example.

It would therefore be an advance in the state of the art to provide a more simple and less expensive process for carbonylation of aromatic halides to prepare aromatic carboxylic acids in excellent yields. It would furthermore be advantageous to provide a simple and efficient method to recover the halide by product in a useable form.

In accordance with the present invention, it has now been found that aromatic iodides can be carbonylated to the desired aromatic carboxylic acids in high yields under mild reaction conditions by the use of the combination of a ruthenium catalyst, a Bronsted base, and an iodide promoter in a carboxylic acid reaction medium. The use of ruthenium as an efficient carbonylation catalyst for aryl halides has not been disclosed or recognized in the prior art. Furthermore, the reaction has high selectivity in the formation of the aromatic carboxylic acid in high purity with little or no formation of products such as aromatic carboxyl aldehydes such as 4-carboxybenzaldehyde or other such compounds even in the presence of large amounts of hydrogen.

The aromatic iodides which may be used in our process may be monoiodo or polyiodo, e.g., di-, tri- and tetra-iodo aromatic compounds. The aromatic nucleus or moiety can contain from 6 to 18 carbon atoms, preferably 6 to 10 carbon atoms and may be carbocyclic aromatic such as benzene, biphenyl, terphenyl, naphthalene, anthracene, etc., or heterocyclic aromatic such as pyridine, thiophene, pyrrole, indole, etc. In addition to one or more iodine atoms, the aromatic moiety may be substituted by various substituents inert under the conditions employed in our process. Examples of such substituents include alkyl of up to about 12 carbon atoms such as methyl, ethyl, isobutyl, hexyl, 2-ethylhexyl, nonyl, decyl, dodecyl, etc.; cycloalkyl of about 5 to 12 carbon atoms such as cyclopentyl, cyclohexyl, 4-butylcyclohexyl, etc.; hydroxy; alkoxy of up to about 12 carbon atoms such as methoxy, ethoxy, propoxy, butoxy, octyloxy, etc.; halogen such as chloro and bromo; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 12 carbon atoms such as vinyl, allyl, etc.; formyl; alkanoyl of about 2 to 8 carbon atoms such as acetyl, propionyl, butyryl, hexanoyl, etc.; alkanoylamido of about 2 to 8 carbon atoms such as acetamido, butylamido, etc.; aroylamino such as benzamido; and alkylsulfonamide such as methanesulfonamide, hexanesulfonamido, etc.

Specific examples of the aromatic iodide reactants include iodobenzene, 1,3- and 1,4-diiodobenzene, 1,3,5-triiodobenzene, 4-iodotoluene, 4-iodophenol, 4-iodoanisole, 4-iodoacetophenone, 4,4'-diiodobiphenyl, 4-chloroiodobenzene, 3-bromoiodobenzene, and 2,6- and 2,7-diiodonaphthalene. Our process is particularly useful for the preparation of benzenedicarboxylic and naphthalenedicarboxylic acids and thus the preferred reactants are diiodobenzenes, especially 1,3- and 1,4-diiodobenzene, and diiodonaphthalenes, especially 2,6- and 2,7-diiodonaphthalene.

The aromatic iodide reactants are known compounds and/or can be prepared according to published procedures. For example, T. Hudlicky et al *The Chemistry of Halides, Pseudohalides and Azides,* Supplement D, Part 2, 1142–1158, the disclosure of which is incorporated herein by reference in its entirety, discloses a number of such processes. Another process described in J. Chem. Soc. 150 (1952) comprises treating an aromatic compound, such as benzene, with iodine in the presence of silver sulfate dissolved in concentrated sulfuric acid.

In the process of this invention, the aromatic iodide is carbonylated in a carboxylic acid reaction medium, such as acetic acid, butyric acid, propionic acid, benzoic acid, and the like or mixtures thereof, with acetic acid being the most preferred. Also, the carbonylation reaction can tolerate substantial quantities of water.

The ruthenium catalyst can be provided to the reaction medium as any of a number of ruthenium salts or complexes that are capable of providing ruthenium in a soluble form in the reaction. Illustrative sources of ruthenium are ruthenium trichloride, ruthenium tribromide, ruthenium triiodide, ruthenium acetate, ruthenium acetylacetonate, ruthenium dioxide, ruthenium tetraoxide, ruthenium pentacarbonyl and dodecacarbonyltriruthenium and their phosphine and halogen substituted analogs. The amount of ruthenium is not significant as long as enough is present to catalyze the reaction. Preferably, the catalyst is present in a concentration of 10 to 0.01 mole percent, preferably 1.0 to 0.1 mole percent, based on the moles of aromatic iodide reactant. Therefore, the total reaction medium has a catalyst concentration of baout 10,000 ppm to 10 ppm with preferred catalyst concentrations of 1000 to 100 ppm.

A Bronsted base is also added to the carboxylic acid reaction medium to maintain and enhance the reaction rate of the carbonylation process. By the term "Bronsted base" we mean any substance that can act as a proton acceptor in the reaction medium. In particular, the Bronsted base can be an acetate, formate, hydroxide, carbonate or alkoxide of an alkali, alkaline earth transition or non-transition metal. The Bronsted base can be added in an amount of about 1 percent to about 15 weight percent, based on the amount of the carboxylic acid reaction medium, preferably about 2 to 10 weight percent. Examples of a Bronsted base are alkali metal carbonates, such as lithium carbonate, as well as alkali metal acetates such as lithium acetate, sodium acetate, potassium acetate and the like, preferably lithium acetate. Alkaline earth metal acetates, such as magnesium acetate, can also be used. Transition and non-transition metal acetates such as iron, manganese, zinc and tin acetates can also be used. Amines such as pyridines and trialkylamines, for example triethylamine or trimethylamine, can be used. Alkali metal acetates can be generated in situ by adding an alkali metal component, such as lithium carbonate, to the carboxylic acid reaction medium such as acetic acid, to form lithium acetate. Also alkyl acetates, such as methyl acetate, can be used when in the presence of an alkali or alkaline earth metal iodide. Alkyl acetates can also be generated in situ by adding an alkanol, such as methanol, to the reaction medium which reacts with the anhydride by-product to form the alkyl acetate.

An alkali or alkaline earth metal iodide which functions as an iodide promoter is also added to the carboxylic acid reaction medium to enhance the carbonylation rate of the carbonylation process. By the term "iodide promoter" we mean an alkali or alkaline earth metal iodide that is capable of providing a soluble form of iodide in the reaction as any number of salts or complexes. Illustrative examples are alkali metal iodides such as lithium iodide, sodium iodide, potassium iodide, rubidium iodide and alkaline earth iodides such as magnesium diiodide, calcium diiodide, strontium diiodide and barium diiodide. The iodide promoter can be added in an amount which results in catalytic activity. Specifically, the amount can be about 0.5 to 25 weight percent, based on the amount of the carboxylic acid reaction medium, preferably 5 to 15 weight percent.

The carbonylation reaction is conducted in the presence of carbon monoxide, which is employed in amounts such that the total reaction pressure is suitable for the formation of the aromatic carboxylic acid. The carbon monoxide employed may be essentially pure or it may contain other gases such as carbon dioxide, hydrogen, methane and other compounds produced by synthesis gas plants. Normally, the carbon monoxide will be at least 90, preferably at least 95, percent pure.

The process of the present invention can be conducted at temperatures and pressures suitable for formation of the aromatic carboxylic acid. The temperatures and pressures are interdependent and can vary considerably. While the process can be carried out at pressures as high as 10,000 psig, the cost of utilities and equipment required for such high pressure operation cannot normally be commercially justified. Thus, the pressure normally will be in the range of about 300 to 4000 psig, preferably about 750 to 1500 psig. A particularly preferred pressure is 1000 psig. While temperatures as low as 125° C. and higher than 225° C. may be used, our process normally is carried out between about 125° to 225° C. The preferred temperature range is 150° to 200° C. A particularly preferred temperature is 175° C.

The process of this invention is particularly useful for the preparation of aromatic dicarboxylic acids such as 1,3- and 1,4-benzenedicarboxylic and 2,6- and 2,7-naphthalenedicarboxylic acids. Such diacids may be used in the preparation of polyesters such as poly(ethylene terephthalate) and poly(ethylene 2,6-naphthalenedicarboxylate).

The process of this invention can be carried out as a batch, semi-continuous or continuous operation. In the manufacture of aromatic dicarboxylic acids in the quantities required for use in the preparation of polyesters such as those mentioned above, the process described hereinabove will be carried out in a continuous manner. A typical continuous method of practicing our process comprises feeding into a mixed pressure vessel a liquid stream composed of 2,6-diiodonaphthalene in acetic acid, the ruthenium catalyst, a Bronsted base, an iodide promoter and a gaseous stream of carbon monoxide. The pressure vessel is equipped with a means for maintaining the desired temperature and pressure. The liquid mixture from the reactor column is centrifuged and 2,6-naphthalene dicarboxylic acid is separated from the solution which is recycled.

The iodide can be recovered from the reaction medium by several methods. For example, when the reaction medium is acetic acid and a stoichiometric amount of metal acetate, such as lithium acetate, is present, acetic anhydride and lithium iodide are formed as reaction by products. Reactive distillation of the acetic anhydride from the lithium iodide containing reaction mixture provides acetyl iodide and lithium acetate. The acetyl iodide can be recovered by distillation. The recovered acetyl iodide can then be hydrolyzed with water to form acetic acid and hydrogen iodide which can be recovered or oxidized to recover the iodide present.

Another method for recovery of the iodide is to add oxygen to the reaction medium which readily oxidizes the iodide to elemental iodine. The elemental iodine can be recovered by distillation, filtration or other suitable means. This method provides a good cost effective and efficient method for iodine recovery whereby the relatively expensive iodine can be recovered and recycled continuously.

Our invention is further illustrated by the following examples. In the procedures utilized in the examples the materials employed are loaded into a 330 ml autoclave constructed of Hastelloy B2 alloy which is designed to operate in a rocking mode. The autoclave is pressurized with 500 psig carbon monoxide gas pressure at room temperature and then the gas is vented and the autoclave is sealed. In these examples the autoclave is pressurized to 250 psig with carbon monoxide gas at ambient temperature and heated and rocked until reaction temperature was reached, at which time additional carbon monoxide gas is added to increase the autoclave internal pressure to the predetermined value. Reactor pressure is maintained by adding carbon monoxide at the same rate at which it is consumed by the reactants. The carbon monoxide used is essentially pure. When the predetermined reaction time is completed the autoclave is cooled by a stream of cold air to approximately 25° C. After the gas is vented from the autoclave the crude product is analyzed by gas chromatographic methods. The % conversion is the mole percent of iodo-group converted to carboxylic acid. The results of these runs are shown below.

| Example No. | 1 | 2 | 3 | 4 | 5 | 6 |
|---|---|---|---|---|---|---|
| Iodoaromatic | iodobenzene | iodobenzene | 2,6/2,7-diiodonaphthalene | iodobenzene | iodobenzene | iodobenzene |
| wt (g) | 50 | 50 | 15 | 61 | 60 | 60 |
| Catalyst | $RuCl_3 \cdot 3H_2O$ | $RuCl_3 \cdot 3H_2O$ | $RuCl_3 \cdot 3H_2O$ | $RuCl_3 \cdot 3H_2O$ | $RuCl_3 \cdot 3H_2O$ | $RuCl_3 \cdot 3H_2O$ |
| wt (g) | 0.50 | 0.50 | 0.50 | 0.50 | 0.50 | 0.50 |
| Base | $Li_2CO_3$ | $Li_2CO_3$ | $Li_2CO_3$ | $Li_2CO_3$ | $Li_2CO_3$ | — |
| wt (g) | 10 | 10 | 10 | 4.0 | 4.0 | — |
| Promoter | LiI | LiI | LiI | LiI | — | LiI |
| wt (g) | 20.0 | 4.0 | 4.0 | 4.0 | — | 4.0 |
| Solvent | acetic acid | acetic acid | acetic acid | acetic acid | acetic acid | acetic acid |
| wt (g) | 156 | 156 | 157 | 155 | 155 | 155 |
| Time (Hr) | 3 | 3 | 3 | 4 | 4 | 4 |
| Pressure (psig) | 1500 | 1500 | 1500 | 1500 | 1500 | 1500 |
| Temp (°C.) | 175 | 175 | 175 | 175 | 175 | 175 |
| % Conversion | 99.5 | 94.3 | 86.6 | 69.5 | 8.2 | 17.0 |

While the invention has been described in detail with particular reference to preferred embodiments thereof, it will be understood that variations and modifications can be effected within the spirit and scope of the invention.

We claim:

1. A process for the production of aromatic carboxylic acids which comprises carbonylating aromatic iodides in the presence of carbon monoxide, a catalytic amount of a ruthenium catalyst, a Bronsted base and a catalytic amount of an alkali or alkaline earth metal iodide under aromatic carboxylic acid forming conditions of temperature and pressure.

2. The process of claim 1 wherein the aromatic iodides are selected from diiodonaphthalene and diiodobenzenes.

3. The process of claim 2 wherein the diiodonaphthalene is 2,6-diiodonaphthalene and the diiodobenzene is 1,4-diiodobenzene.

4. The process of claim 1 wherein the temperature is in the range of about 125° to 225° C.

5. The process of claim 4 wherein the temperature is in the range of about 150°–200° C.

6. The process of claim 1 wherein the pressure is in the range of 300 to 4000 psig.

7. The process of claim 6 wherein the pressure is in the range of 750 to 1500 psig.

8. The process of claim 1 wherein the alkali metal iodide is selected from the group consisting of lithium iodide, sodium iodide, potassium iodide and rubidium iodide.

9. The process of claim 1 wherein the alkaline earth metal iodide is selected from the group consisting of magnesium diiodide, calcium diiodide, strontium diiodide and barium diiodide.

10. The process of claim 1 wherein the Bronsted base is selected from the group consisting of acetates, formates, hydroxides, carbonates and alkoxides of alkaline earth, alkali, transition and non-transition metals.

11. The process of claim 10 wherein the Bronsted base is an alkali metal carbonate.

12. A process for the production of aromatic discarboxylic acids selected from benzene discarboxylic acids and naphthalene dicarboxylic acids which comprises carbonylating a diiodobenzene or a diiodonaphthalene in the presence of carbon monoxide, lithium carbonate, a catalytic amount of a ruthenium catalyst, and a catalytic amount of lithium iodide at a temperature of about 150° to 200° C. and a pressure of about 750 to 1500 psig.

13. A process for the production of 2,6-naphthalenedicarboxylic acid which comprises carbonylating 2,6-diiodonaphthalene in the presence of carbon monoxide, lithium carbonate, a catalytic amount of ruthenium, and a catalytic amount of lithium iodide at a temperature of about 175° C. and a pressure of about 1000 psig.

* * * * *